United States Patent [19]

Davey

[11] Patent Number: 5,055,465

[45] Date of Patent: Oct. 8, 1991

[54] IMIDAZOQUINOXALINONES, THEIR AZA ANALOGS AND PROCESS FOR THEIR PREPARATION

[75] Inventor: David D. Davey, Succasunna, N.J.

[73] Assignee: Berlex Laboratories, Inc., Cedar Knolls, N.J.

[21] Appl. No.: 359,182

[22] Filed: May 31, 1989

[51] Int. Cl.$^5$ .................. A61K 31/54; A61K 31/535; C07D 417/14; C07D 413/14

[52] U.S. Cl. .............................. 514/228.2; 514/233.2; 514/250; 544/60; 544/80; 544/115; 544/346

[58] Field of Search .................. 514/228.2, 233.2, 250; 544/60, 80, 81, 115, 346

[56] References Cited

U.S. PATENT DOCUMENTS 4,333,394 6/1982 Barnes et al. .

4,440,929 3/1984 Lee et al. .

OTHER PUBLICATIONS

Synthesis and Oral Antiallergic Activity of Carboxylic Acids derived from Imidazo—etc. —Ager et al., J. Med. Chem., 1988, 31, 1098–1115.

*Primary Examiner*—Mary C. Lee
*Assistant Examiner*—Joseph K. McKane
*Attorney, Agent, or Firm*—Elizabeth A. Bellamy; John L. White; I. William Millen

[57] ABSTRACT

This invention relates to novel imidazoquinoxalinones and their aza analogs and to a process for their preparation. The compounds of this invention have been found to have inodilatory, vasodilatory, venodilatory and other pharmacologic effects.

25 Claims, No Drawings

IMIDAZOQUINOXALINONES, THEIR AZA ANALOGS AND PROCESS FOR THEIR PREPARATION

FIELD OF THE INVENTION

This invention relates to novel imidazoquinoxalinones, their aza analogs and their pharmaceutically acceptable salts. Further encompassed by the invention is a novel process for the production of the imidazoquinoxalinones and their aza analogs. The compounds of the invention exhibit a variety of pharmacological properties for which pharmaceutical compositions are proposed.

GENERAL DESCRIPTION OF THE INVENTION

Composition-of-Matter Aspect

In its composition-of-matter aspect, this invention relates to novel imidazoquinoxalinones, their aza analogs and the pharmaceutically acceptable salts thereof.

Compounds encompassed by the invention are of the following Formula I:

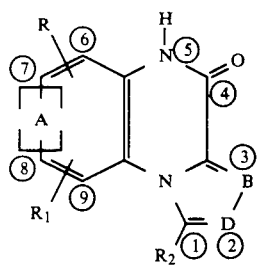

wherein

A is N or CH; B is N or CR, and D is N or $CR_2$.

R, $R_1$, are the same or independently hydrogen, hydroxy, loweralkyl, lower alkoxy, phenyloxy, $R_6S(O)n$-, W-ALK-Q-,

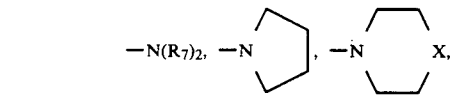

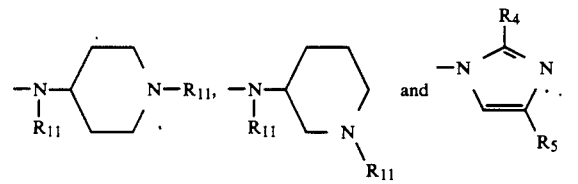

$R_2$ is hydrogen, lower alkyl, phenyl which may be substituted by up to three methoxy groups, lower alkyl substituted by phenyl which may be substituted by up to three methoxy groups, —lower alkyl —$N(R_8)_2$,

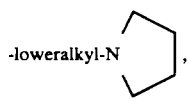

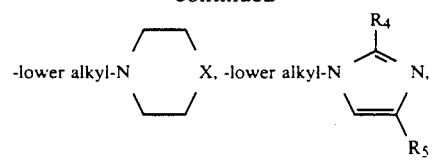

pyridinyl or loweralkyl pyridinyl.

$R_3$ is hydrogen, lower alkyl, phenyl, lower alkylphenyl, pyridinyl or loweralkyl pyridinyl.

$R_4$, $R_5$ are the same or independently hydrogen or lower alkyl.

$R_6$ is lower alkyl, phenyl, lower alkylphenyl or pyridinyl.

$R_7$ are the same or independently hydrogen, loweralkyl, phenyl, pyridinyl,

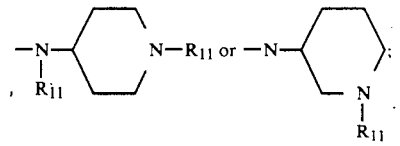

$R_8$ are the same or independently lower alkyl, phenyl or pyridinyl.

$$Q \text{ is } -O-, -\underset{R_9}{N}-, -CH_2O- \text{ or } -CH_2\underset{R_9}{N}-,$$

W is hydroxy, loweralkoxy, phenoxy, $-N(R_{10})_2$,

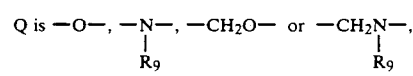

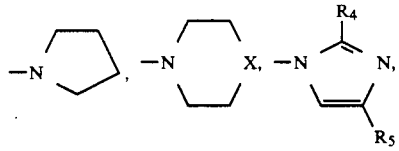

ALK is a $C_1$-$C_4$ straight or branched chain alkyl;
$R_9$ is hydrogen, lower alkyl or phenyl;
$R_{10}$ are the same or independently hydrogen, loweralkyl or phenyl;
$R_{11}$ are the same or independently hydrogen or lower alkyl;
X is $CH_2$, O, $S(O)_n$, $-NR_{10}$;
n is the integer 0, 1 or 2 and
p is the integer 0 or 1.

Inclusive of the compounds of Formula I are the provisos that:
a) one and only one of B or D must be N;
b) when A is CH, when D is N, when B is $CR_3$ where $R_3$ is H, when $R_2$ is hydrogen, lower alkyl or phenyl then R and/or $R_1$ must be

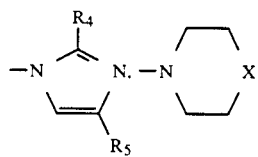

or W—ALK—Q—;

As used herein, the term "lower" when used conjunctively with alkyl or alkoxy shall represent a straight or branched chain alkyl of one to four carbon atoms as for example methyl, ethyl, propyl, isopropyl, butyl, sec-butyl, isobutyl and tertiary butyl.

Also contemplated as part of this invention are the pharmaceutically acceptable salts of the compounds of Formula I. These may be acid or base addition in nature. The acid addition salts may be formed with inorganic or organic acids. Illustrative but not restrictive examples of such acids include hydrochloric, hydrobromic, sulfuric, phosphoric, citric, methanesulfonic, 2-hydroxyethanesulfonic, toluenesulfonic, benzenesulfonic, camphorsulfonic and ethanesulfonic acids. The base addition salts may be formed with the metal ions as for example, sodium, potassium or calcium.

It is to be understood that the definition of the compounds of Formula I encompasses all possible steroisomers and mixtures thereof, which possess the activities discussed below. In particular, it encompasses the geometrical and optical isomers and the racemic modifications thereof which possess the indicated activity.

As stated previously, the compounds of the invention have been found to exhibit a variety of pharmacologic effects. More particularly, various species have been shown to have inodilator, vasodilator or venodilator activities.

Preferred classes of compounds which exhibits inodilator effects are those of Formula I with the following characteristics:
1) when
   A is N or CH;
   and R is H;
   $R_1$ is H,

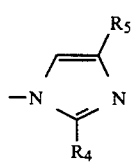

at the 7 position,

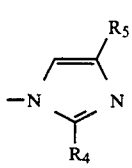

at the 8 position,

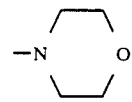

at the 8 position or —$SO_2R_6$ at the 8 position;

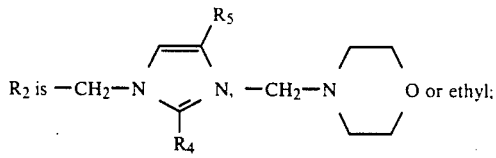

2) when B is N and $R_2$ is phenyl or ethyl;
3) when B is $CR_3$ and $R_3$ is methyl.

Preferred classes of compounds of Formula I which exhibit vasodilator effects are those of the following characteristics:
1) when A is N or CH,
   R is ethyl or propyl at the 6 position;
   $R_1$ is

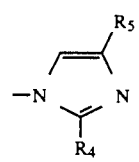

at the 7 or 8 position, —$SO_2CH_3$ at the 8 position or

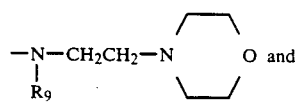

$R_2$ is ethyl or propyl.
2) when B is N and $R_2$ is phenyl.
3) when B is $CR_3$ and $R_3$ is H or methyl.

Preferred classes of compounds of Formula I which exhibit venodilator - particularly anti-anginal effects are those of the following characteristics:
1) when
   A is N,
   R is

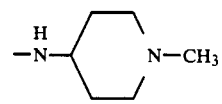

at the 6 position,

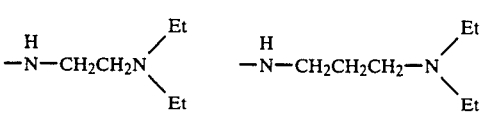

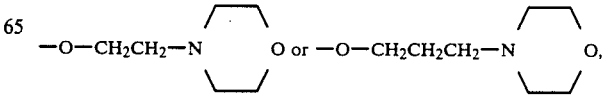

$R_1$ is H. 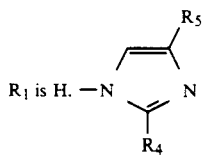

at the 8 position,

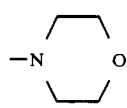

at the 8 position or —SO$_2$CH$_3$ at the 8 position;
$R_2$ is ethyl or propyl.

2) when B is N and $R_2$ is hydrogen or phenyl.

3) when B is CR$_3$ and $R_3$ is hydrogen or CH$_3$.

The following compounds are some of those which serve to exemplify the various composition-of-matter and/or process aspects of the invention as described herein.

1) 1,2-Dimethylimidazo[1,2-a]pyrido[5,6-e]pyrazin-4(5H)-one.
2) 7,9-Dimethyl-2-(thiomorpholin-4-yl)imidazo[1,5-a]pyrido[2,3-e]-pyrazin-6(5H)-one.
3) 8-(4-(2-Propyl)piperazin-1-yl)imidazol[1,2-a]quinoxalin-4(5H)-one.
4) 1-Ethyl-8-(2-diethylamino)ethoxyimidazo[1,5-a]quinoxalin-4(5H)-one.
5) 7-(1H-Imidazol-1-yl)imidazol[1,2-a]pyrido[4,5-e]pyrazin-4(5H)-one.
6) 7-Methylimidazo[1,5-a]pyrido[2,3-e]pyrazin-6(5H)-one.
7) 1-Ethyl-8-(1H-imidazol-1-yl)-3-methyl-6-(2-(morpholin-4-yl)ethoxy)-imidazo[1,5-a]quinoxalin-4(5H)-one.
8) 1,6-Diethyl-3-methyl-3-(methylsulfonyl)imidazo[1,5-a]quinoxalin-4(5H)-one.
9) 8-(1H-Imidazol-1-yl)-6-(2-(morpholin-4-yl)ethoxy)-3-phenylimidazo-[1,2-a]quinoxalin-4(5H)-one.
10) 1-(2-Ethyl-1H-imidazol-1-yl)methyl-6-methoxymethylimidazo[1,5-a]-quinoxalin-4(5H)-one.
11) 1-Ethyl-2-methyl-6-(2-(morpholin-4-yl)ethoxy)methylimidazo[1,5-a]-quinoxalin-4(5H)-one.
12) 6-[(((2-Dimethylamino)ethyl)methylamino)methyl]-2-(pyridin-3-yl)-imidazo[1,2-a]quinoxalin-4(5H)-one.
13) 1-Ethyl-6-[((2-(morpholin-4-yl)ethyl)amino)methyl]imidazo[1,2-a]-quinoxalin-4(5H)-one.

PROCESS ASPECT

The novel imidazoquinoxalinones and their aza analogs, the subject of this invention, are prepared essentially as illustrated in the following schemes A and B - which schemes are inclusive of a novel ultimate or pentultimate cyclization step.

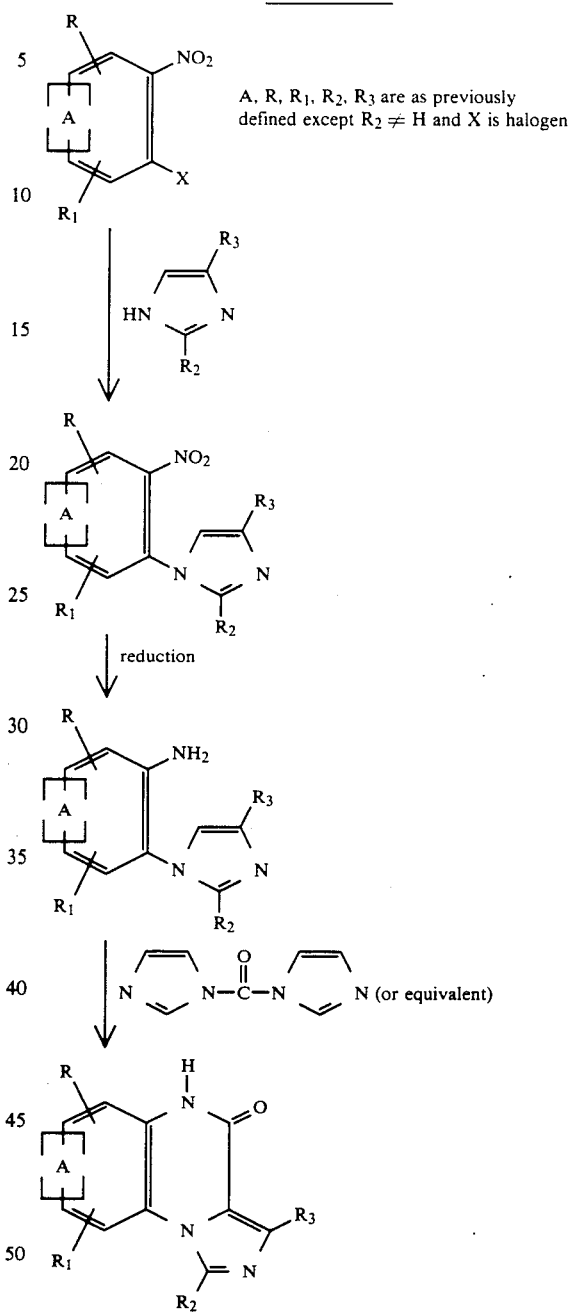

SCHEME A

A, R, $R_1$, $R_2$, $R_3$ are as previously defined except $R_2 \neq$ H and X is halogen

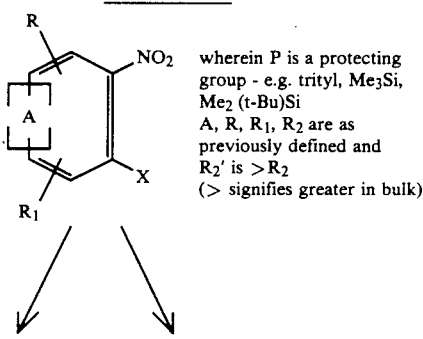

SCHEME B wherein P is a protecting group - e.g. trityl, Me$_3$Si, Me$_2$(t-Bu)Si
A, R, $R_1$, $R_2$ are as previously defined and $R_2'$ is > $R_2$
(> signifies greater in bulk)

-continued
SCHEME B

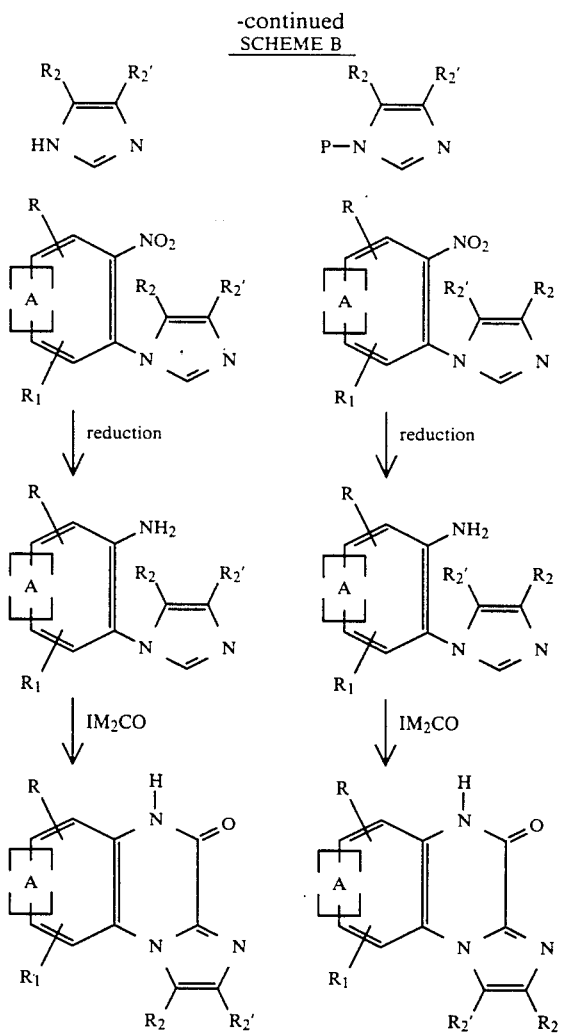

As illustrated in the foregoing schemes, treatment of an appropriately substituted ortho halo nitro aromatic (prepared by standard methods known in the art) with a substituted or non-substituted imidazole in an aprotic solvent (acetonitrile, dimethyl sulfoxide, dimethyl formamide or methylene chloride) at temperatures ranging from about 0° to about 150° C. gives the ortho imidazol-1-yl nitro aromatic. In the case of 4 and 4,5 substituted imidazoles, attack by the less hindered nitrogen of the imidazole leads to the major product. Attack by the more hindered nitrogen can be achieved by protecting the least hindered nitrogen with a trityl group prior to the displacement reaction. The by-product of this reaction is trityl halide.

Reduction of the nitro group to an amino group is readily achieved with either tin chloride or catalytic hydrogenation. The choice of either reagent is normally dictated by the chemical stability of the various substituents.

The cyclization procedures known in the art are not sufficient to prepare the compounds of this invention. As for example, the cyclization techniques as utilized in U.S. Pat. No. 4,440,929 would not allow B in Formula I to be nitrogen but more importantly, when B in Formula I is $CR_8$, $R_3$ could not be lower alkyl, phenyl or loweralkylphenyl and $R_2$ could only be H.

The novel cyclization process of this invention is reacting a compound of the following Formula II:

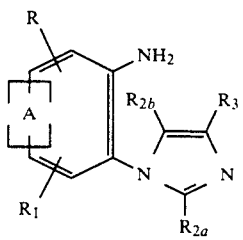

wherein R, $R_1$ & $R_3$ have the same meaning as in Formula I and wherein $R_{2a}$ and $R_{2b}$ have the same meaning as $R_2$ and where one of $R_{2a}$ or $R_{2b}$ must be hydrogen; with 1 to 4 equivalent excess of a doubly activated carbonic acid derivative in an inert aprotic solvent at a temperature of from about 150° C. to about 200° C. for about 30 minutes to 6 hours.

The doubly activated carbonic acid derivative is selected from carbonyldiimidazole, diphenyl carbonate, phosgene or an equivalent, preferably carbonyldiimidazole. The aprotic solvent is selected from N-methylpyrollidinone, tetralin, decalin, 1,2-dichlorobenzene, 1,3-dimethyl-2-imidazolidinone, preferably 1,2-dichlorobenzene. The temperature of the reaction is preferably 170°-180° C. with a reaction duration of about 1-4 hours.

After the reaction is completed, the reaction mixture is cooled and the final products extracted with aqueous acid or base dependent on the substituents present. The final products are further purified by crystallization or column chromatography.

As can be ascertained, if the 2 ($R_{2a}$) position of the imidazole is unsubstituted, the cyclization occurs at this position to give the 1,2-a ring system, likewise, when the 2 ($R_{2a}$) is substituted and the 5-($R_{2b}$) position is unsubstituted, cyclization occurs at the 5 ($R_{2b}$) position to give the 1,5-a ring system.

METHOD-OF-USE AND PHARMACEUTICAL COMPOSITION ASPECT

Compounds in this series have actions as positive inotropic/vasodilators, mixed (arterial and venous) vasodilators, and selective venodilators. Agents which have both positive inotropic and vasodilating actions have utility in the treatment of congestive heart failure, supporting the failing heart both by increasing its pump function and by decreasing the load against which it must work. Mixed vasodilators reduce both preload and afterload on the heart and thus have utility in congestive heart failure; in addition, such agents have utility in the treatment of angina pectoris, hypertension, and other disorders of the circulation. Venodilators, which selectively decrease the preload on the heart, have utility in the treatment of angina pectoris and congestive heart failure.

The following procedure was used for the initial identification of compounds having vasodilator activity. Such compounds would be useful for the treatment of hypertension or heart failure. The compounds were evaluated by assessing vasodilator activity in rings of canine coronary artery or mesenteric vein in vitro.

Dogs of either sec were anesthetized with pentobarbital (35 mg/kg, i.v.). The heart and mesentery were removed and placed in oxygenated (95% $O_2$/5% $CO_2$) physiological salt solution (PSS) at 37° C. The circumflex coronary artery and the mesentric vein were dissected free from the adventitia, cut into segments of approximately 2 mm in length, mounted on muscle holders, and placed into 20 ml organ baths filled with PSS, with oxygenation and temperature maintained as above for study under isometric conditions. Optimum preload for each ring was determined with 20 mM KCl followed by a 30 min relaxation period.

Tissues were checked for endothelial competence by contracting the rings with 20 mM KCl (arteries) or 2 μM phenylephrine (veins) and then challenging with 1 μM acetylcholine or 2 Y thrombin, respectively. A relaxation of at least 65% was considered acceptable. The vessels were then washed free of drugs and allowed to relax for 30 min.

For compound testing, the coronary artery rings were contracted with 50 nM, 9,11-dideoxy-11α,9α-epoxymethano-prostaglandin Fα (U46619), and the mesenteric veins were contracted with 2 μM phenylephrine. These concentrations were chosen to provide approximately 50% of the maximum contraction attainable. Test compounds were added beginning 5 min after the contraction had reached a plateau. Additions were made cumulatively as log doses over the concentration range of 10 nM to 100 μM. Successive doses were added to the bath at 10 min intervals or when the previous response had reached a plateau.

After the last dose of test agent, the tissues were washed repeatedly every 10 min until complete relaxation was obtained. Tissue viability and endothelium competence was then verified by recontracting the vessels with the prostaglandin (arteries) or phenylephrine (veins) and challenging with acetylcholine or thrombin, respectively, as above.

The compounds were tested for their inodilator activity, that is for usefulness as cardiotonic agents, in the ferret papillary muscle contractility model which model is published in J. Med. Chem. 1987, 30, 1347.

Total effective vascular compliance was measured in pentobarbitalanesthetized dogs pretreated with atropine, propranolol, and hexamethonium to block reflex responses and using a sustained infusion of norepinephrine to increase central venous pressure to approximately 5 mm Hg. Animals were instrumented for the measurement of left ventricular pressure, aortic pressure, and central venous pressure. Measured volumes of blood were infused and withdrawn and changes in central venous pressure were monitored (see Stewart, D. J., Elsner, D., Sommer, O., Holtz, J, and Bassenge, E. Circulation 74:573–582, 1986).

Total effective vascular compliance was expressed as the reciprocal of the slope of the volume-pressure curve. This model measures the compliance of the total vascular bed, but, since 85% of the total compliance lies on the venous side, experimental results largely reflect actions on the venous side.

Because the compounds exhibit inodilator, vasodilator or venodilator activity, it is envisioned that they would be useful as broncodilators, antiallergics, diuretics or topical agents for the treatment for baldness.

The compounds of the invention can be administered orally or parenterally. The dosage and method of administration will be dependent on the age, weight, sex and other characteristics of the subject to be treated and the disease state or states to be treated. The compounds when administered orally or parenterally will be admixed with non-toxic pharmaceutically acceptable carriers in accordance with standard pharmaceutical practices taking into account the compound/s to be administered, the dosage form and disease state/s to be effected.

The invention described hereinabove is illustrated below in the Preparations and Examples which, however, is not to be construed as limiting the invention.

PREPARATIONS

Preparation 1

2-(4-Morpholinyl)methyl-1-(2-nitrophenyl)imidazole

Combine 10 g of 2-fluoronitrobenzene, 13 g of 2-((4-morpholinyl)methyl)-imidazole, 18 mL of N,N-diisopropyl ethylamine, and 150 mL of acetonitrile, and heat at reflux for 48 hr. Remove the solvent under vacuum, and dissolve the residue in 500 mL of 2N $H_2SO_4$. Wash the aqueous portion with 400 mL of ether, basify with $K_2CO_3$, and extract with two 400 mL portions of $CH_2Cl_2$. Combine extracts, dry over $MgSO_4$, charcoal treat and remove the solvent under vacuum to provide the title compound.

Preparation 2

2-Ethyl-1-(2-nitro-5-fluorophenyl)-4-methyl-1H-imidazole

Combine 100 g of 2,4-difluoronitrobenzene, 69 g of 2-ethyl-4-methylimidazole and 100 g of $K_2CO_3$ in 700 mL of acetonitrile, and stir at room temperature for 4 days. Remove the solvent under vacuum. Slurry the residue in 300 mL of $CH_2Cl_2$ and chromatograph over 1 kg of silica gel using $CH_2Cl_2$. Combine the appropriate fractions and remove the solvent under vacuum. Crystallize the residue from pet ether to provide the title compound.

NMR ($CDCl_3$):δ1.20(t,3), 2.25(s,3), 2.44(q,2), 6.59(s,1), 7.3(d,1), 7.30(m,1), and 8.09(m,1) ppm.

Preparation 3

In a manner similar to Preparation 2, the following compounds can be prepared:

A) 2-methyl-1-(2-nitro-5-fluorophenyl)-1H-imidazole and

B) 2-ethyl-1-(2-nitro-5-fluorophenyl)-1H-imidazole.

Preparation 4

2-[2-((Morpholin-4-yl)methyl)-1H-imidazol-1-yl]benzeneamine

Combine 7 g of the compound of Preparation 1 and 0.5 g of 10% palladium on carbon in 200 mL of ethanol, and hydrogenate at 50 psi for 3 h. Remove the catalyst by filtration and concentrate the filtrate in vacuo. Crystallize the residue from ether to provide the title compound.

NMR ($CDCl_3$):δ2.35(d,4), 3.40(d,2), 3.59(m,4), 3.90(s,2), 6.81(m,2), 6.98(s,1), 7.09(m,2), and 7.25(m,1)ppm.

EXAMPLES

EXAMPLE 1

1-((Morpholin-4-yl)methyl)imidazo[1,5-a]quinoxalin-4(5H)-one

Combine 5 g of the compound of Preparation 4 and 3.5 g of 1,1'-carbonyldiimidazole in 150 mL of 1,2-dichlorobenzene and heat at reflux under $N_2$ for 2 h. Cool to room temperature, filter the precipitate and wash with acetone to provide the title compound:

NMR (DMSO):δ2.50(m,4), 3.56(m,4), 4.03(s,2), 7.28(m,3), 7.80(s,1), 8.23(d,1), and 11.47(s,1)ppm.

In a manner similar to Example 1, the following compounds may be prepared:

EXAMPLE 2

8-(1H-Imidazol-1-yl)imidazo[1,2-a]quinoxalin-4(5H)-one

Prepare by reaction of 2,4-difluoronitrobenzene with excess imidazole, following by reduction with $H_2$/Pd-C and cyclization with carbonyldiimidazole to provide the title compound.

NMR (CF$_3$CO$_2$D):δ7.98(s,1), 7.99(m,3), 8.28(s,1), 8.76(m,2) and 9.23(s,1)ppm.

EXAMPLE 3

1-Methyl-8-(2-methyl-1H-imidazol-1-yl)imidazo[1,5-a]quinoxalin-4(5H)-one

Prepare by reaction of 2,4-difluoronitrobenzene with excess 2-methylimidazole followed by reduction with H$_2$Pd-C and cyclization with carbonyldiimidazole to provide the title compound.

NMR (DMSO):δ2.35(s,3), 2.95(s,3), 6.94(s,1), 7.40(m,3), 7.77(s,1), 7.97(s,1) and 9.5(s,1)ppm.

EXAMPLE 4

2-(1H-Imidazol-1-yl)imidazo[1,2-a]pyrido[2,3-e]pyrazin-b 6(5H)-one

Prepare by reaction of 2,6-dichloro-3-nitropyridine with excess imidazole followed by hydrogenation with palladium on carbon and cyclization with carbonyldiimidazole to provide the title compound.

NMR (DCl/D$_2$O):δ7.78(d,1), 8.23(m,2), 8.44(m,2), 8.94(d,1) and 9.83(d,1)ppm.

EXAMPLE 5

9-Methyl-2-(2-methyl-1H-imidazol-1,5-a]pyrido[2,3-e]pyrazin-6(5H)-one

Prepare by reaction of 2,6-dichloro-3-nitropyridine with excess 2-methylimidazole followed by hydrogenation with Pd-C, and cyclization with carbonyldiimidazole to provide the title compound.

NMR (DMSO):δ2.51(s,3), 2.96(s,3), 6.96(s,1), 7.56(s,1), 7.61(d,1), 7.79(s,1) and 7.82(d,1)ppm.

EXAMPLE 6

Imidazo[1,2-a]pyrido[2,3-e]pyrazin-6(5H)-one

Prepare by reaction of imidazole with 2-chloro-3-nitropyridine followed by hydrogenation with Pd-C and cyclization with carbonyldiimidazole to provide the title compound.

NMR (CF$_3$CO$_2$D):δ7.87(m,1), 8.23(m,2), 8.78(d,1), and 8.91(s,1)ppm.

EXAMPLE 7

9-Ethylimidazo[1,5-a]pyrido[2,3-e]pyrazine-6(5H)-one

Prepare by reaction of 2-chloro-3-nitropyridine with 2-ethylimidazole followed by hydrogenation with palladium on carbon and cyclization with carbonyldiimidazole to provide the title compound.

NMR (DMSOδ1.33(t,3), 3.42(q,2), 7.41(m,1), 7.65(m,2), and 8.24(d,1) ppm.

EXAMPLE 8

1-Ethylimidazo[1,5-a]pyrido[4,5-e]pyrazine-4(5H)-one

Prepare by reaction of 3-fluoro-4-nitropyridine-N-oxide with 2-ethylimidazole followed by hydrogenation with Pd-C and cyclization with carbonyldiimidazole to provide the title compound.

NMR (DMSO):δ1.39(t,3), 3.28(q,2), 7.26(d,1), 7.35(s,1), 8.42(d,1) and 9.16(s,1) ppm.

EXAMPLE 9

9-(2-Ethyl-1H-imidazol-1-yl)methylimidazo[1,5-a]pyrido[2,3-e]pyrazin-6(5H)-one

Prepare by treatment of 2-chloro-3-nitropyridine with 2-(2-ethyl-1H-imidazol-1-yl)methyl-1H-imidazole followed by hydrogenation with Pd-C and cyclization with carbonyldiimidazole to provide the title compound.

NMR (DMSO)δ1.84(t,3), 2.71(q,2), 5.96(s,2), 6.70(s,1), 6.98(s,1), 7.43(m,1), 7.71(d,1), 7.80(s,1), and 8.25(d,1) ppm.

EXAMPLE 10

8-Phenylimidazo[1,2-a]pyrido[2,3-e]pyrazin-6(5H)-one

Prepare by treatment of 2-chloro-3-nitropyridine with 4-phenylimidazole followed by hydrogenation with Pd-C and cyclization with carbonyldiimidazole to provide the title compound.

NMR (CF$_3$CO$_2$D):δ7.63(m,5), 7.90(m,2), 8.03(d,1), and 8.61(d,1) ppm.

EXAMPLE 11

1-Ethyl-8-(2-ethyl-4-methyl-1H-imidazol-1-yl)-3-methylimidazo[1,5-a]quinoxalin-4(5H)-one Prepare by treatment of 2,4-difluoronitrobenzene with excess 2-ethyl-4-methylimidazole followed by hydrogenation with Pd-C and cyclization with carbonyldiimidazole to provide the title compound.

NMR (DMSO):δ1.12(t,3), 1.35(t,3), 2.15(s,3), 2.51(s,3), 2.55(q,2), 3.20(q,2), 7.09(s,1), 7.38(s,2), and 7.83(s,1) ppm.

EXAMPLE 12

1-Ethyl-3-methyl-8-(pyrolidin-1-yl)imidazo[1,5-a]quinoxalin-4(5H)-one

Treat the compound of Preparation 2 with pyrolidine followed by hydrogenation with palladium on carbon and cyclization with carbonyldiimidazole to provide the title compound.

NMR (DMSO):δ1.38(t,3), 1.97(m,4), 2.51(s,3), 3.21(m,6), 6.55(d,1), 7.00(s,1), and 7.12(d,1) ppm.

EXAMPLE 13

1-Ethyl-3-methyl-8-(morpholin-4-yl)imidazo[1,5-a]quinoxalin-4(5H)-one

Treat the compound of Preparation 2 with morpholine followed by hydrogenation with Pd-C and cyclization with carbonyldiimidazole to provide the title compound.

NMR (DMSO):δ1.36(t,3), 2.51(s,3), 3.11(m,4), 3.23(q,2), 3.76(m,4), 7.00(d,1), 7.15(d,1), and 7.35(s,1) ppm.

EXAMPLE 14

1-Ethyl-8-(1H-imidazol-1-yl)-3-methylimidazo[1,5-a]quinoxalin-4(5H)-one

Treat the compound of Preparation 2 with imidazole followed by hydrogenation with palladium on carbon and cyclization with carbonyldiimidazole to provide the title compound.

NMR (CF$_3$CO$_2$D):δ1.68(t,3), 2.94(s,3), 3.69(q,2), 7.76(m,4), 8.30(s,1), and 9.19(s,1) ppm.

EXAMPLE 15

8-(1H-Imidazol-1-yl)-1-methylimidazo[1,5-a]quinoxalin-4(5H)-one

Treat the compound of Preparation 3A with imidazole followed by hydrogenation with Pd-C and cyclization with carbonyldiimidazole to provide the title compound.

NMR (DMSO):δ3.04(s,3), 7.15(s,1), 7.41(d,1), 7.63(q,1), 7.76(m,2), 8.08(d,1), and 8.39(s,1) ppm.

EXAMPLE 16

1-Ethyl-8-(1H-imidazol-1-yl)imidazo[1,5-a]quinoxalin-4(5H)-one

Treat the compound of Preparation 3B with imidazole followed by hydrogenation with Pd-C and cyclization with carbonyldiimidazole to provide the title compound.

NMR (DMSO):δ1.41(t,3), 3.41(q,2), 7.19(s,1), 7.44(m,1), 7.62(m,2), 8.04(d,1) and 8.28(s,1) ppm.

EXAMPLE 17

1-(1H-Imidazol-1-yl)methyl-8-(N-phenyl-(4-hydroxybutyl)amino)imidazo-[1,5-a]pyrido[3,4-e]pyrazin-4(5H)-one Treat 2,4-dichloro-5-nitropyridine with 2-((imidazol-1-yl)methyl)imidazole followed by reaction with N-phenyl-4-hydroxybutylamine, hydrogenation with palladium on carbon and cyclization with carbonyldiimidazole to provide the title compound.

EXAMPLE 18

1-Ethyl-2-methyl-6-(2-(morpholin-4-yl)ethoxymethylimidazo[1,5-a]-quinoxalin-4(5H)-one Treat 3-fluoro-2-nitrobenzaldehyde with 2-ethyl-4-methyl-imidazole. Follow with palladium catalyzed hydrogenation to the amino alcohol. Alkylate with sodium hydrode and 4(2-chloroethyl)morpholine and cyclize with carbonyldiimidazole to provide the title compound.

EXAMPLE 19

1-Ethyl-6-[((2-(morpholin-4-yl)ethyl)amino)methyl]imidazo[1,2-a]-quinoxalin-4(5H)-one Treat 3-fluoro-2-nitrobenzoic acid methylester with 1-trityl-4-ethyl imidazole, followed by treatment with 4-(2-aminoethyl)morpholine and catalytic hydrogenation cyclization with carbonyldiimidazole, followed by reduction with lithium aluminum hydride to provide the title compound.

Contemplated as equivalents to the compounds of this invention are the triazoloquinoxalinones and their aza analogs of the following Formula III.

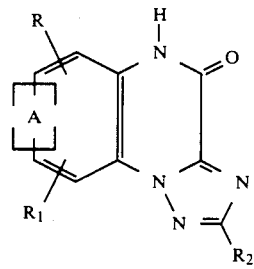

where A, R, R$_1$ and R$_2$ and the pharmaceutically acceptable salts take the same meaning as in Formula I. The compounds of Formula III can be prepared in the same manner as depicted in Scheme A except that the imidazole reactant becomes the following:

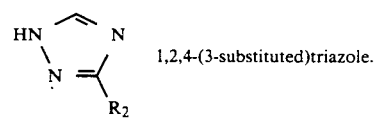

1,2,4-(3-substituted)triazole.

Formula III compounds are exemplified, for example, triazolo[1,5a]-pyrido[3,2-e]pyrazin-6(5H)-one and 6-(2-(1H-imidazol-1-yl)ethyl)amino-2-phenyltriazolo[1,5-a]quinoxalin-4(5H)-one and others.

I claim:
1. A compound of the following Formula I:

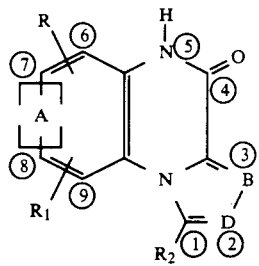

wherein
A is N or CH;
B is N or CR$_3$;
D is N or CR$_2$;
R, R$_1$, are the same or independently hydrogen, hydroxy, loweralkyl, lower alkoxy, phenyloxy, R$_6$S(O)$_n$-, W-ALK-Q-,

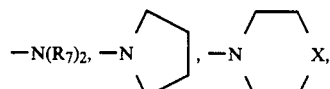

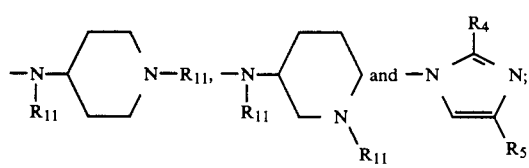

R$_2$ is hydrogen, lower alkyl, phenyl which may be substituted by up to three methoxy groups, lower alkyl substituted by phenyl which may be substituted by up to three methoxy groups, —lower alkyl —N(R$_8$)$_2$,

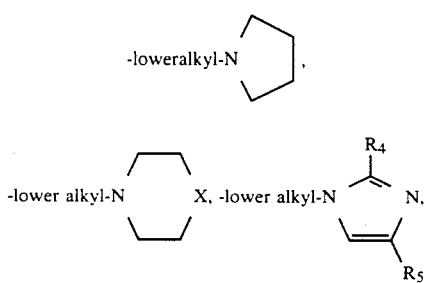

pyridinyl or loweralkyl pyridinyl;

R₃ is hydrogen, lower alkyl, phenyl, lower alkylphenyl, pyridinyl or loweralkyl pyridinyl;

R₄, R₅ are the same or independently hydrogen or lower alkyl;

R₆ is lower alkyl, phenyl, lower alkylphenyl or pyridinyl;

R₇ are the same or independently hydrogen, loweralkyl, phenyl, pyridinyl,

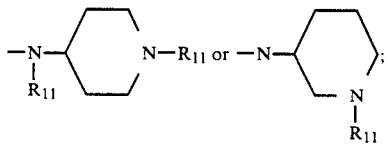

R₈ are the same or independently lower alkyl, phenyl or pyridinyl;

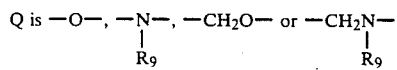

W is hydroxy, loweralkoxy, phenoxy, —N(R₁₀)₂,

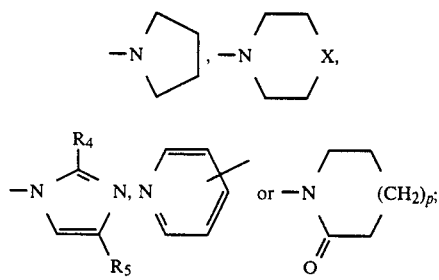

ALK is a $C_1$–$C_4$ straight or branched chain alkyl;

R₉ is hydrogen, lower alkyl or phenyl;

R₁₀ are the same or independently hydrogen, loweralkyl or phenyl;

R₁₁ are the same or independently hydrogen or lower alkyl;

X is —CH₂—, —O—, S(O)$_n$, —NR₁₀;

n is the integer 0, 1 or 2 and p is the integer 0 or 1.

with the provisos that:

a) one and only one of B or D must be N;

b) when A is CH, when D is N, when B is CR₃ where R₃ is H, when R₂ is hydrogen, lower alkyl or phenyl then R and/or R₁ must be

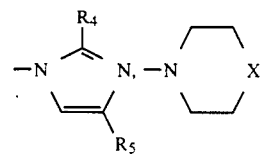

or W—ALK—Q—;

and the pharmaceutically acceptable salts thereof.

2. A compound of claim 1 where A is CH, B is CR₃ and D is N.

3. A compound of claim 1 where A is CH, D is CR₂ and B is N.

4. A compound of claim 1 where A and D are N and B is CR₃.

5. A compound of claim 1 where A and B are N and D is CR₂.

6. A compound of claim 2 which is 1-ethyl-8-(1H-imidazol-1-yl)-3-methylimidazo[1,5-a]quinoxalin-4(5H)-one.

7. A compound of claim 2 which is 1-ethyl-8-(1H-imidazol-1-yl)imidazo-[1,5-a]quinoxalin-4(5H)-one.

8. A compound of claim 2 which is 1-ethyl-3-methyl-8-(4-morpholino)-imidazo[1,5-a]quinoxalin-4(5H)-one.

9. A compound of claim 2 which is 1-ethyl-8-(2-ethyl-4-methyl-1H-imidazol-1-yl)-3-methylimidazo[1,5-a]quinoxalin-4(5H)-one.

10. A compound of claim 2 which is 1-methyl-8-(2-methyl-1H-imidazol-1-yl)imidazo[1,5-a]quinoxalin-4(5H)-one.

11. A compound of claim 2 which is 8-(1H-imidazol-1-yl)-1-methylimidiazo[1,5-a]quinoxalin-4(5H)-one.

12. A compound of claim 2 which is 1-ethyl-3-methyl-8-(pyrrolidin-1-yl)imidazo[1,5-a]quinoxalin-4(5H)-one.

13. A compound of claim 2 which is 1-((morpholin-4-yl)methyl)imidazo[1,5-a]quinoxalin-4(5H)-one.

14. A compound of claim 2 which is 6-ethoxy-1-ethyl-8-(2-ethyl-4-methyl-1H-imidazol-1-yl)-3-methylimidazo[1,5-a]quinoxalin-4(5H)-one.

15. A compound of claim 3 which is 8-(1H-imidazol-1-yl)imidazo[1,2-a]quinoxalin-4(5H)-one.

16. A compound of claim 3 which is imidazo[1,2-a]quinoxalin-5-(4H)-one.

17. A compound of claim 3 which is 2-methylimidazo[1,2-a]quinoxalin-4(5H)-one.

18. A compound of claim 4 which is 9-ethylimidazo[1,5-a]pyrido[3,2-e]pyrazin-6(5H)-one.

19. A compound of claim 4 which is 9-methyl-2-(2-methyl-1H-imidazol-1-yl)imidazo[1,5-a]pyrido[3,2-e]pyrazin-5(6H)-one.

20. A compound of claim 4 which is 9-[(2-ethyl-1H-imidazol-1-yl)methyl]imidazo[1,5-a]pyrido[3,2-e]pyrazin-6(5H)-one.

21. A compound of claim 4 which is 1-ethylimidazo[1,5-a]pyrido[4,3-e]-pyrazin-4-(5H)-one.

22. A compound of claim 5 which is imidazo[1,2-a]pyrido[3,2-e]pyrazin-6(5H)-one.

23. A compound of claim 5 which is 2-phenylimidazo[1,2-a]pyrido[2,3-e]pyrazin-4(5H)-one.

24. A compound of claim 5 which is 2-(1H-imidazol-1-yl)imidazo[1,2-a]pyrido[3,2-e]pyrazin-6(5H)-one.

25. A pharmaceutical composition comprising at least one compound according to claim 1, together with one or more non-toxic pharmaceutically acceptable carriers.

* * * * *

UNITED STATES PATENT AND TRADEMARK OFFICE
CERTIFICATE OF CORRECTION

PATENT NO. : 5,055,465
DATED : October 8, 1991
INVENTOR(S) : David D. Davey

It is certified that error appears in the above-identified patent and that said Letters Patent is hereby corrected as shown below:

Column 1, line 39

"B is N or CR" should read
--- B is N or $CR_3$ ---

Column 5, line 32

"imidazol [1,2-a]" should read
--- imidazo [1,2-a] ---

Column 5, line 38

"imidazol [1,2-a]" should read
--- imidazo [1,2-a] ---

Column 5, line 46

"3-methyl-3-" should be
--- 3-methyl-8- ---

Column 7, line 65

"when B in Formula I is $CR_8$," should read
--- when B in Formula I is $CR_3$, ---

UNITED STATES PATENT AND TRADEMARK OFFICE
CERTIFICATE OF CORRECTION

PATENT NO. : 5,055,465

DATED : October 8, 1991

INVENTOR(S) : David D. Davey

It is certified that error appears in the above-identified patent and that said Letters Patent is hereby corrected as shown below:

Column 8, line 64

"Dogs of either sec" should read
--- Dogs of either sex ---

Column 9, line 11

"or 2 Y thrombin" should read
--- or 2 U thrombin ---

Column 11, line 30

"[2,3-e]pyrazinb-6(5H)" should read
--- [2,3-e]pyrazin-6(5H) ---

Column 11, line 40

"(2-methyl-1H-imidazol-1,5-a]" should read
--- (2-methyl-1H-imidazol-1-yl)imidazo[1,5-a] ---

Column 11, line 67

"NMR (DMSO $\delta$" should read
--- NMR (DMSO) $\delta$ ---

UNITED STATES PATENT AND TRADEMARK OFFICE
CERTIFICATE OF CORRECTION

PATENT NO. : 5,055,465
DATED : October 8, 1991
INVENTOR(S) : David D. Davey

It is certified that error appears in the above-identified patent and that said Letters Patent is hereby corrected as shown below:

Column 13, line 52

"with sodium hydrode" should read
--- with sodium hydride ---

Column 16, line 33

"imidiazo[1,5-a]" should read
--- imidazo[1,5-a] ---

Signed and Sealed this

Fourteenth Day of September, 1993

Attest:

BRUCE LEHMAN

Attesting Officer

Commissioner of Patents and Trademarks